United States Patent [19]
Adler et al.

[11] Patent Number: 6,023,495
[45] Date of Patent: Feb. 8, 2000

[54] SYSTEM AND METHOD FOR ACQUIRING THREE-DIMENSIONAL DATA SUBJECT TO PRACTICAL CONSTRAINTS BY INTEGRATING CT SLICE DATA AND CT SCOUT IMAGES

[75] Inventors: Roy Lee Adler, Chappaqua; Alan David Kalvin, Irvington; Joseph Y. Margulies, Armonk; Charles P. Tresser, Marmaroneck; Chai Wah Wu, Ossining, all of N.Y.

[73] Assignee: International Business Machines Corporation, Armonk, N.Y.

[21] Appl. No.: 09/079,515

[22] Filed: May 15, 1998

[51] Int. Cl.⁷ .......................................... A61B 6/03
[52] U.S. Cl. ................. 378/4; 378/901; 382/131
[58] Field of Search ........................ 378/4, 901; 382/131

[56] References Cited

U.S. PATENT DOCUMENTS 4,630,203  12/1986  Szirtes ..................................... 382/132

Primary Examiner—David Vernon Bruce
Attorney, Agent, or Firm—Whitham, Curtis & Whitham; Louis J. Percello

[57] ABSTRACT

A computer system and method solve the problem of getting a useful three-dimensional representation of an object like the spine using a small amount of data. This is done by gathering and combining three-dimensional data in the form of (a) a set of 2D computer tomography (CT) slices of a patient's bones with (b) a set of 2D CT scout images, which are digital two-dimensional X-ray images that can be produced by a CT scanner. The main features of spinal deformation are captured by integrating these two sets of three-dimensional data, and constructing from them a three-dimensional geometric model of the spinal. Scouts are usually used to monitor CT scan acquisition. Here, they are also used as an essential source of data.

5 Claims, 9 Drawing Sheets

SYSTEM AND METHOD FOR ACQUIRING THREE-DIMENSIONAL DATA SUBJECT TO PRACTICAL CONSTRAINTS BY INTEGRATING CT SLICE DATA AND CT SCOUT IMAGES

CROSS REFERENCE TO RELATED APPLICATION

The subject matter of this application is related to that of U.S. patent application Ser. No. 09/025,677 filed Feb. 18, 1998, filed by Alan David Kalvin for "System and Method for Reducing Reconstruction Artifacts in Computed Tomography Images" and assigned to a common assignee herewith. The disclosure of application Ser. No. 09/025,677 is incorporated herein by reference.

BACKGROUND OF THE INVENTION

1. Field of the Invention

The present invention generally relates to the field of computer image processing of computer tomography (CT) images and, more particularly, to the problem of acquiring three-dimensional geometry of large objects, using X-ray based methods, subject to practical constraints such as limited radiation dosage and limited scanning time.

2. Background Description

U.S. Pat. No. 5,416,815, which is incorporated here by reference in its entirety, describes computer tomography (CT) systems and the method of image reconstruction from projections. The usefulness of getting three-dimensional (3D) representations of objects under study has long been recognized, in particular, in medicine. Several techniques, more or less invasive, have been developed which allow three dimensional data acquisition. The present invention addresses the case when data acquisition techniques are so invasive that their use has to be minimized. Thus, one has to rely on a limited amount of information gathering to construct a useful three-dimensional rendering of the object of study.

Although the principles disclosed here are applicable to quite general settings, medical or otherwise, we will concentrate on the study of the spine of patients afflicted with idiopathic scoliosis. Idiopathic scoliosis is a condition which affects a very large bone structure, the spine. Since X-ray analysis is commonly used in the study of bones, the size of the spine and the limited amount of X-ray that a patient can withstand, prohibit fine X-ray computer tomography (CT) scanning as a method to get a three-dimensional representation. Furthermore, the evolutive nature of the condition implies that examinations have to be frequently repeated, with accumulative radiation hazard, which is another reason to look for small doses of radiation in the process of data acquisition.

Idiopathic scoliosis is a little understood disease. It is a progressive three-dimensional (3D) deformation of the spine involving curvature and torsion which affects about 3% of adolescents, one fifth of whom require extensive medical testing to determine whether dramatic and dangerous surgery will be required. A general reference on scoliosis can be found in *Moe's Textbook of Scoliosis and Other Spinal Deformities* by John E. Lonstein, David S. Bradford, Robert B. Winter and James Ogilvie, 3rd edition, W. B. Saunders & Co., 1995. Many authors have tried to explain the possible etiology of scoliosis. The term "idiopathic", means "different suffering" in Greek: "idiopathic scoliosis" has the sense of "enigmatic scoliosis".

Scoliosis, in general, is a major deformity that involves practically the whole musculo-skeletal system, and probably other systems as well. Attempts to explain the phenomenon have led to some nosological successes in which a minority of patients have been diagnosed as suffering from something other than idiopathic scoliosis. For that disease, however, the mystery remains. How can a major pathological process that changes practically the whole body go unexplained, with an undetected source? This comprises probably one of the most fascinating enigmas of medicine.

Severe scoliosis leads to one of the grandest surgical procedures known to medicine. The primary goal of surgery is to prevent further deterioration, the secondary one is to correct the deformity as much as is still possible. Spinal fusion is the current treatment. It has absolutely nothing to do with the basic etiology and pathophysiology of the disease and does not attempt to treat its cause. It is a crude mechanical approach which can often lead to subsequent problems. Nevertheless, until a better solution is found, it is the best option.

Definitions

The basic concepts described in the present invention are better understood with review of the following definitions.

PIXEL: A picture element. The basic element in a two-dimensional (2D) digital picture.

IMAGE: A rectangular 2D digital picture. Each pixel in the image is identified by a pair of integers (x,y), where x and y are the column and row locations of the pixel respectively. (We shall use the terms "slice" and "image" interchangeably in describing the present invention).

CT Slice: A 2D cross-sectional image of a 3D object that is produced by a CT scanner.

CT Table Position: Associated with each CT slice is a value known as the slice's "table position" which is the position of the CT scanner table at the time the slice data were acquired. This value is used to determine the position of the 2D slice within the 3D object being scanned.

IMAGE SEGMENTATION: The process of identifying objects of interest in an image.

EDGE: An edge is a point in an image at the transition between two regions having markedly disparate pixel values.

SEGMENTED OBJECT: A object of interest in an image identified by the process of segmentation.

The following definitions are made with reference to FIG. 8.

RAY: This refers to a single X-ray beam 801 that travels from the CT scanner X-ray tube 802 to a detector cell on the CT scanner detector 803 array.

VIEW: A view 804 consists of a set of rays 801 produced by a CT scanner with the X-ray tube 802 in a fixed position.

SINOGRAM: In its standard mode of operation, a CT scanner collects a set S of views while the CT table is held in a fixed position. The views in the set S are acquired at different positions of the X-ray tube as it rotates around the table. A sinogram consist of all the projection data (or a processed version thereof) in a single set S of views.

Since each data point in a sinogram corresponds to a single ray traveling from the X-ray source to the detector, we can represent a sinogram as a 2D image, where each pixel is uniquely identified by the ordered pair of integers (r,v) where v is the view containing this ray, and r is the number of the ray within view v. We will therefore use the following terms interchangeably: sinogram data; projection data; sinogram image; projection image.

SCOUT IMAGE: A scout image is a 2D digital X-ray produced when a CT machine scans a collection of objects while the X-ray tube is held in a fixed position, and the CT table, together with the objects, is moved.

Problems to be Solved

The spine is an extremely complex object consisting of twenty-four vertebrae, which are themselves complicated objects, separated by disks. One must get a simpler geometric representation of the full spine which will capture the essential aspects of the three-dimensional information involved in idiopathic scoliosis. In the present disclosure we shall provide a means of obtaining three-dimensional geometric data of vertebral bodies and their relative positions from X-ray data. The result will allow the practitioner to obtain all the measurements available in previous art as well as a better understanding of the three-dimensional deformation of the spine.

Several authors have reported on difficulties associated with data acquisition and processing and representing the deviation of a pathological spine from a healthy one. These difficulties are twofold:

1) How to limit radiation dosage: On one hand, there is the unavoidable need to get as much information as possible, using methods both reliable and as uninvasive as possible. Unbearably heavy doses of radiation would be needed to obtain sufficient information for reasonable calculations with most present time approaches, e.g., high resolution CT scans, while other modes of imaging like MRI or ultra sounds are inherently not appropriate for the problem at hand.

2) How to extract three-dimensional measurements from 2D X-ray images: On the other hand, we want to avoid the inaccuracy induced by the conventional X-ray based measurements, which depend on two-dimensional projections of a three-dimensional deformity on a celluloid sheet. Some of the difficulties in this category are somehow artificial resulting from lack of universally accepted protocol of measurement (see, e.g., W. Skalli, F. Lavaste, and J. L. Descrimes, "Quantification of three-dimensional vertebral rotations in scoliosis: what are the true values?", Spine, 20 (1995), 546–553). The basic problem here is the inconsistency in definition of parameters of the deformed vertebrae on the two-dimensional display. Reference measurement points on the vertebrae, needed for calculations of correction, are ambiguously describable as reported for instance in references B. Drerup, "Improvement in measuring vertebral rotations from the projections of the pedicles", J. Biomechanics, 18 (1985), 369–378, B. Xion, B. Sevastik, J. Sevastik, R. Hedlund, I. Suliman, and S. Kristjansson, "Horizontal plane morphometry of normal and scoliotic vertebrae", Eur. Spine J., 4 (1995), 6–10, T. Kojima and T. Kurokawa, "Quantification of three-dimensional deformity of idiopathic scoliosis", Spine, 17 (1992), S22–S29, and H. Labelle, J. Dansereau, C. Bellefleur, and J. S. Jaquier, "Variability of geometric measurements from three-dimensional reconstructions of scoliotic spines and rib cages", Eur. Spine J., 4 (1995), 88–94.

SUMMARY OF THE INVENTION

It is therefore an object of the present invention to provide a system and method to solve the problem of getting useful three-dimensional representation of an object like the spine using a limited amount of data.

According to the invention, we solve this problem by integrating three-dimensional CT scans of a patient's anatomy with three-dimensional data derived from CT scout images (or scouts). Scouts are digital two-dimensional X-ray images produced by a CT scanner. They are usually used to plan and monitor CT scan acquisition. In this invention, we use them as an essential source of quantitative data. In an alternative embodiment of this invention standard two-dimensional X-ray images could be used. In this case, they would first need to be digitized, and their scanning geometry registered with that of the CT scan data.

In the test case of spinal examination of patients afflicted by idiopathic scoliosis, we can capture the salient features of the spinal deformation by combining CT scan data and the scout data.

More particularly, according to the invention, to solve problem one (i.e., how to limit radiation dosage), we constrain the CT scanning to acquiring just a small number of slices. Of course, by limiting the amount of radiation dosage, by limiting the amount of CT data acquired, we have also limited the amount of three-dimensional data we have available form CT scanning.

This problem is solved by addressing problem two (i.e., how to extract three-dimensional measurements from 2D X-ray images). In the preferred embodiment of this invention the 2D X-ray images are scout images. Since scout images are produced by the same device (the CT scanner) that produced the CT slices, both types of data (CT slices and scout images) are automatically registered; i.e., their positions in 3D are described in the same coordinate frame. Since the scout data are a form of X-ray projection data, we can apply standard tomographic reconstruction algorithms to create additional 2D cross-sectional slices of the 3D object that has been scanned. These 2D slices are then combined with the original slices produced directly by the CT scanner to provide a 3D volume of data from which the geometry of 3D object is derived.

Each 2D slice in the (relatively) large set of scout-derived slices typically contain less detail and more noise than each of 2D slices coming from the (relatively) small set of high-resolution CT slices. However the combined sets of slices provides sufficient detail for tasks such as visualization for treating spinal scoliosis.

The reason for this can be seen by noting that while it is difficult to quantify how much a deformed vertebra has moved out of its healthy position, the amount of internal vertebral deformation is irrelevant in quantifying the difference between the pathological position and the planned surgical correction. Thus, instead of trying to get high-resolution geometric details, this invention provides a way to get sufficient geometric details of deformed vertebrae and the spine as a whole, while keeping radiation dosage to acceptable levels. Note that the practitioner will still be able to extract conventional measurements such as the Cobb angle (see Cobb, J. R. "Outline for study of scoliosis", American Academy of Orthopedics and Surgery, vol. 7, pp. 160 et seq., 1948), but will not be limited to these very partial estimators of the disease.

By keeping radiation dosage low, this invention can be used for repeatedly acquiring spinal geometry from a single scoliotic patient, and thus provides a way to trace the evolution of the patient's condition over time with far more precision than can be done with prior art methods. Nevertheless, it avoids the high radiation level that would be required from repeatedly acquiring spinal geometry using large sets of (high-resolution) CT slices.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
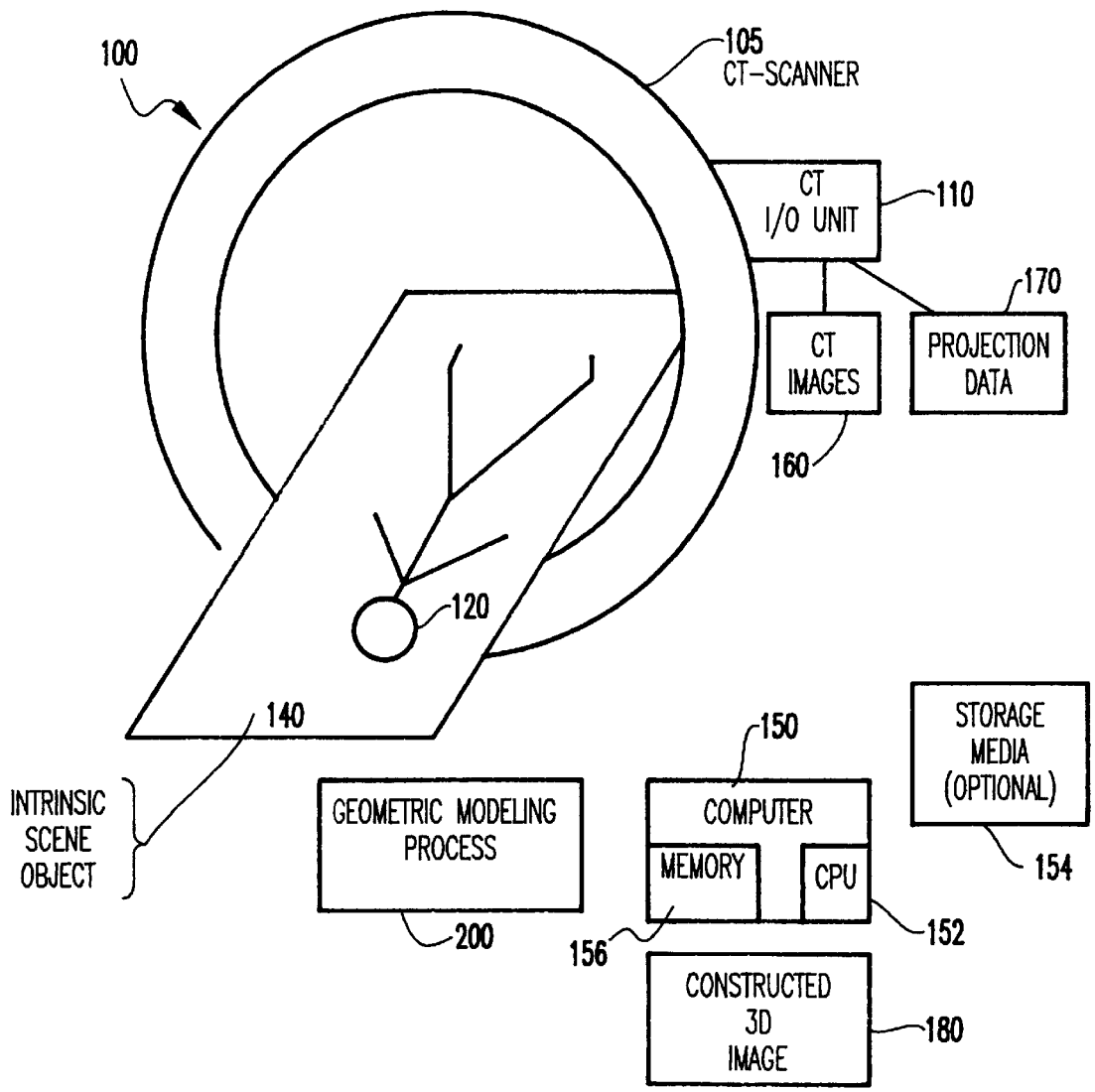
FIG. 1 is a block diagram of a computer tomography (CT. system using the present invention.

Referring now to the drawings, and more particularly to FIG. 1, there is shown one preferred embodiment of the present invention for accessing the three-dimensional geometry of large objects in computer tomography (CT) images 160 produced by a computed tomography scanner 105. A patient 120 is scanned by the CT scanner 105, collecting projection data 170 from the CT input/output (I/O) unit 110, from which is created a set of two-dimensional CT images 160. This process of creating the images 160 is known as image reconstruction from projections. The CT images 160 contain cross-sectional details of the scene that was scanned, which typically includes the patient 120.

The CT images 160 and the related CT projection data 170 are input to a computer 150 and, optionally, stored on an external storage medium 154. The computer 150 may be, for example, an IBM RISC System 6000 workstation running AIX, IBM's version of the UNIX operating system, and the external storage medium 154 may be, for example, a disk storage system connected to the computer. The computer 150 includes a central processing unit (CPU) 152 and memory 156.

A geometric modeling program 200 stored in memory 156 running on CPU 152 of the computer 150 reads in the CT images 160 and projection data 170, and then:
1) computes a set of 2D slices from the scout data,
2) integrates into a single 3D volume of data
   i) the scout-derived slices, and
   ii) the original CT slices, and
3) extracts from this 3D volume a geometric model of the 3D object of interest (e.g. the patient's spine).

We now describe the full process of acquisition of a three-dimensional geometric model of a patient's spine. This model can easily be incorporated in a visualization tool such as IBM's Data Explorer to provide a three-dimensional picture of the twenty-four vertebral bodies as they are located in space.

Intertwining Complete and Intermediate Examinations

If the problem of radiation doses could be ignored, the CT scan technology by itself would allow to obtain high accuracy of the three-dimensional geometry of the spine solely on the basis of techniques which are now of current use. We disclose here a method to get satisfactory geometric understanding of the (diseased) spine with far less radiation than the prohibitive amount that would be required for a systematic CT scan exploration.

Although our procedure involves quite reduced radiation doses, it is natural to aim at even less. While we attempt to use as little data as possible at this stage, further reductions will be possible in some cases, more reduction being expected as practitioners gather and exchange more and more data obtained by our method. To explain this, we need first to describe the typical examination plan.

In the case of timely detection, a patient would be examined every six months from ages two to eighteen, except during the about two years long growth spurt when examinations are made every three or four months. On the average, this amounts to thirty-five radiological examinations. These examinations will be divided into two classes; the complete examinations and the intermediate examinations. In practice, there will be about eight complete examinations.

The complete examinations would involve our most extensive data acquisition. Based on the fact that the global spine geometry evolves faster than the individual vertebral shapes, the geometric models obtained from the data collected during the complete examinations will be used to get pictures of the spine from a smaller amount of data obtained during the intermediate examinations. The intermediate examinations are performed between the complete examinations. The two kinds of examinations are intertwined so that one always has a satisfactory representation both of the spine and of the individual vertebrae while using as little radiation as possible.

In the preferred embodiment of the invention, we use CT scout images. These which could be replaced by traditional X-rays; however, the use of CT scouts is preferable to that of classical X-rays for the following reasons:
(1) it involves far less radiation that usual X-rays thanks to the fact that the data are recorded by detectors instead of an emulsion on celluloid;
(2) the data are directly available in digital form;
(3) at least one scout is needed anyhow for CT scans monitoring; and
(4) the scouts are always mutually co-registered and are co-registered with the CT scans, where geometrical data A is co-registered with geometrical data B if they are acquired in the same reference frame.

The description of the collection of data in the preferred embodiment involves CT scan machines for supine patients as this is the current state of the art. This description would adapt readily to examinations where the patient is erect, as soon as such CT scan machines are available (the erect position might be preferable as it is closer to traditional examinations).

We will divide the vertebrae into two classes: deformed vertebrae and transitional vertebrae. Deformed vertebra consist of the apical vertebrae and those next to the apices, where the deviation from normality is not only in the solid motion in space, but also in the deformation of the bone structure. Transitional vertebrae deviate (if at all) from normality mainly by their solid displacement in space and present at most minor deformations of the bone structure.

Data to be Collected During Complete Examinations

We describe here the data to be collected during the complete examinations as defined above. There will usually be up to eight such examinations in the history of the patient.

D1 A set of CT scout images. In the preferred embodiment of this invention, between four and eighteen scout images are used. In general this number can be whatever the practitioner finds will give him the best tradeoff between lowering radiation dosage and lowering the precision of the geometric model derived from the scouts and CT slices combined).

D2 Two CT cuts per transitional vertebra, at about one third and two thirds of the height. (However, one may suffice.)

D3 Several 1 millimeter (mm) thick CT cuts (as is commonly used for three-dimensional reconstruction) for deformed vertebrae.

Figure 2:
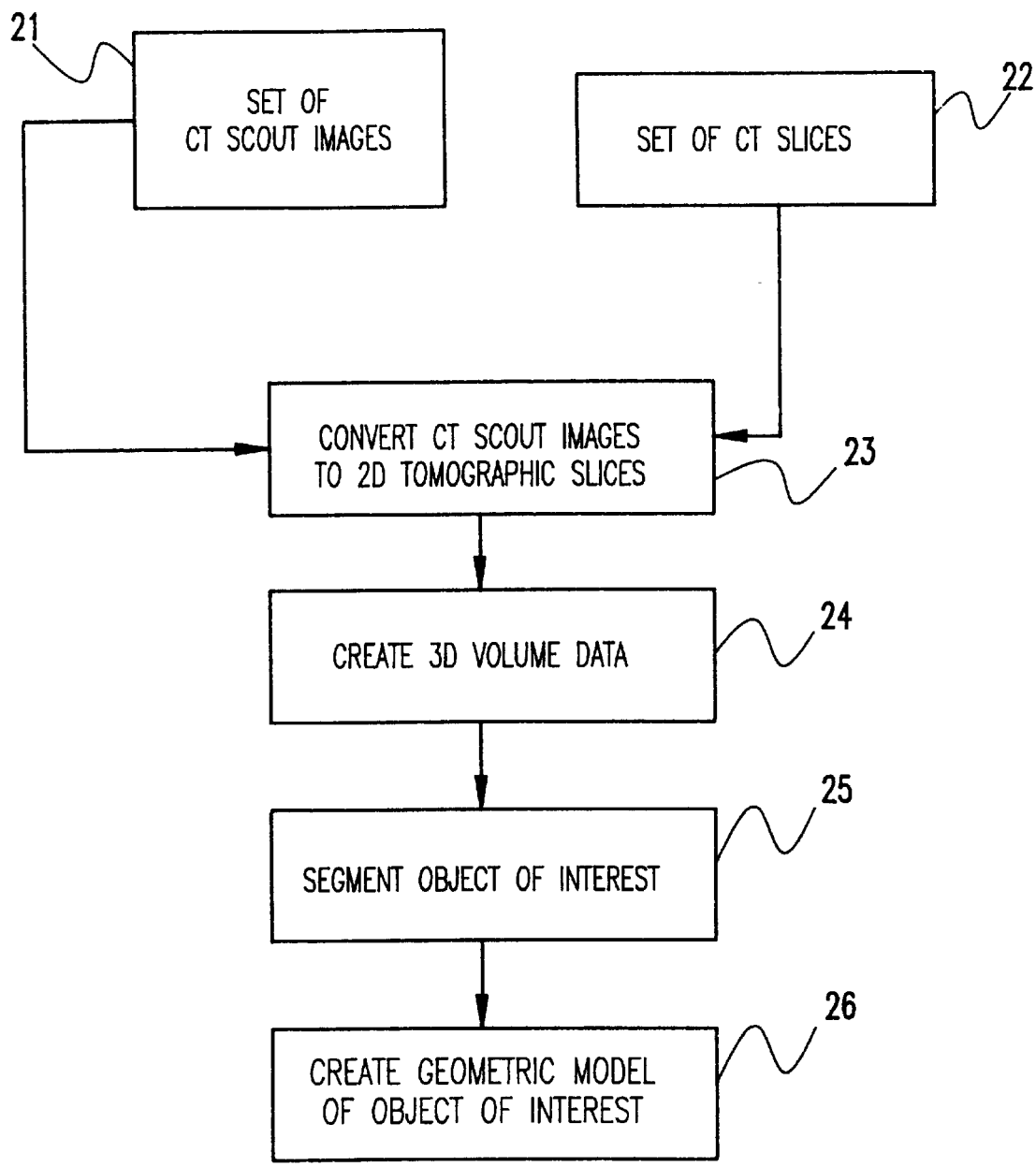
FIG. 2 is a flow chart showing the overall logic of the computer implemented process according to the invention.

FIG. 2 is a flow chart showing the overall logic of the process according to the invention implemented on the computer system shown in FIG. 1. In FIG. 2, there are two sets of data. The first, at input block 21, is a set of co-axial 2D CT scout images, and the second, at input block 22, is a set of 2D CT slices. The set of CT scout images is converted to 2D tomographic slices in function block 23. A 3D volume of data is created in function block 24 by interleaving the set of scout-derived tomographic slices and the set of CT slices. Now, an object of interest is segmented in function block 25. Finally, a geometric model of the object of interest is created in function block 26.

Figure 3:
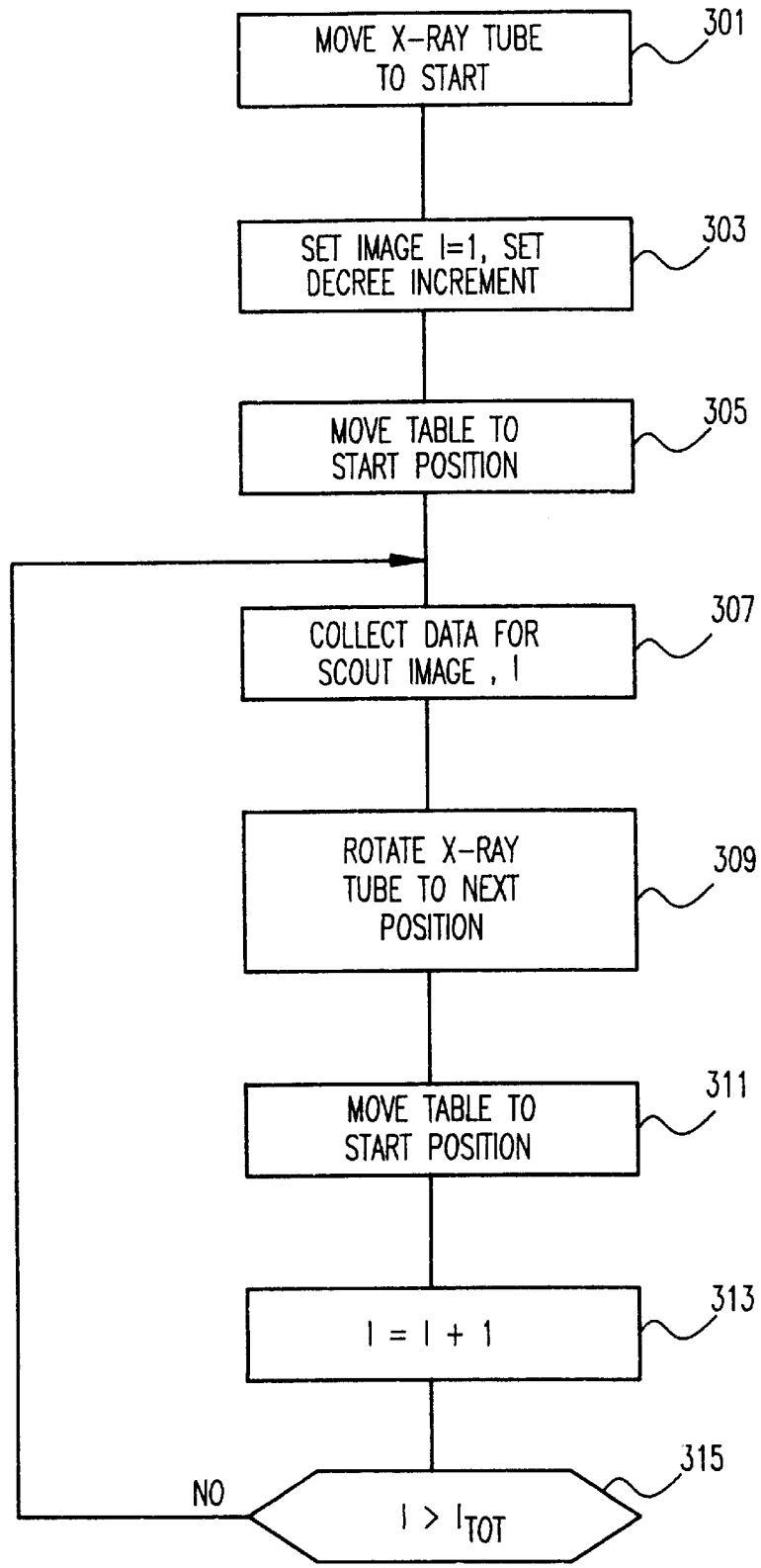
FIG. 3 is a flow chart of the steps for collecting scout data for the inventive method.

FIG. 3 is a flow chart of the steps of the inventive method of collecting scout data (i.e., step D1 above). The X-ray tube is moved to a start position, as is shown in the step in block 301. At the same time the degree increment is set. The degree increment refers to the setting of the X-ray around a 360° radius. The setting of degree increments determines the total number of images, I_TOT, collected. For instance, it the degree increment is set for 36°, then the total number of images collected will be 10 (360°/36°=10). Then, the image number, I, is set to 1 as shown in the step in block 303. As shown in the step in block 305, the table on which the object is positioned is moved to a start position. Then, as shown in the step in block 307, the data for scout image, I, is collected. This step is performed by moving the table from the start position to an end position and recording data at detectors at fixed time intervals, such as every 1/10 of a second. After the scout image data are collected the X-ray tube is rotated to the next position, as shown in the step in block 309. Then, in the step as shown in block 311 the table is moved to the start position. Then, as shown in the step in block 313, the image number I is reset by adding 1. Next, as shown in the step in block 315, the image number, I is evaluated to determine if it is greater than the total number of images to be collected. If no, the process loops back to collecting data for the scout image, I, in the step in block 307. If yes, the data collecting process is complete.

Figure 4:
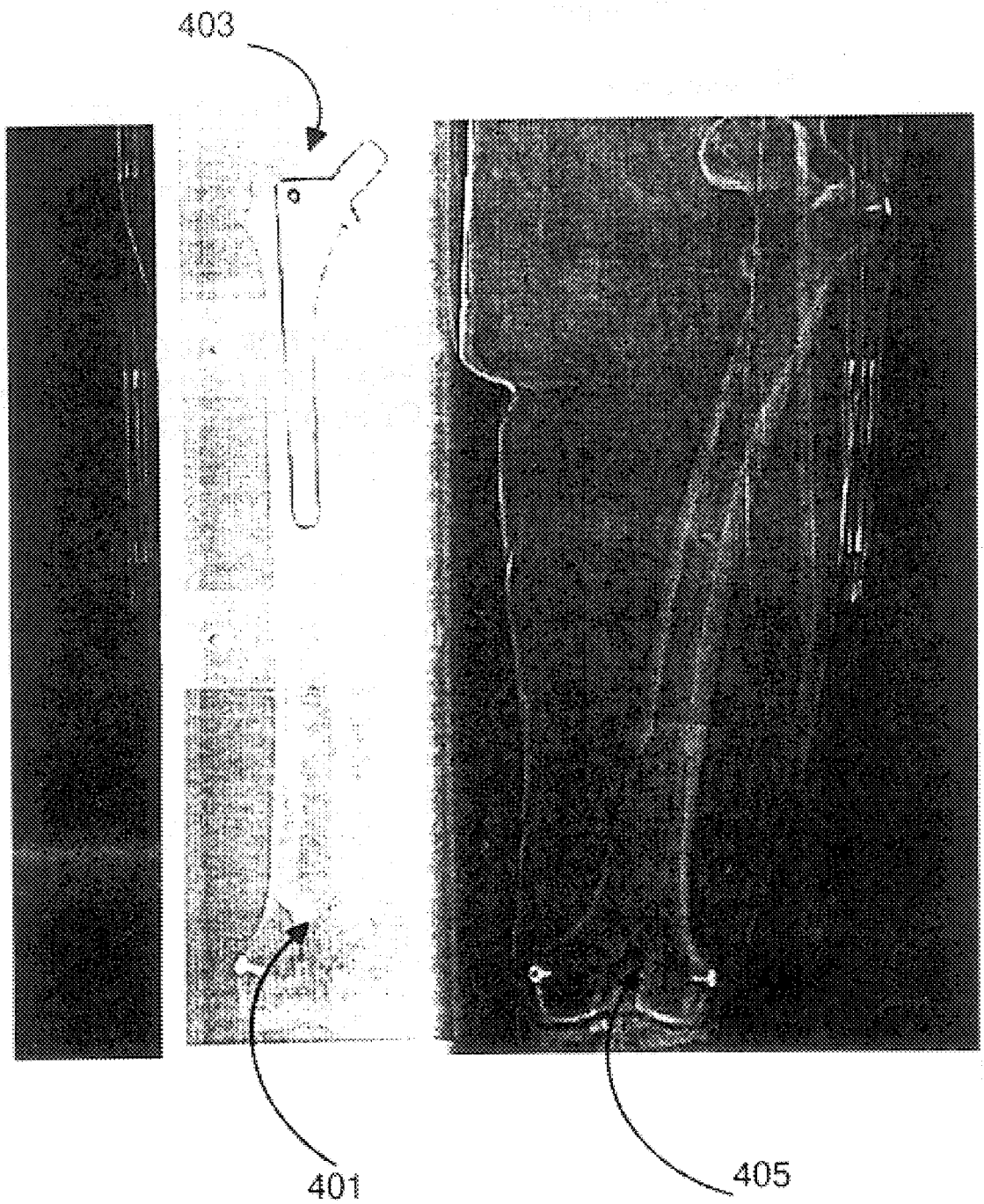
FIG. 4 is a typical scout image.

FIG. 4 shows a scout image of a scanning phantom consisting of a cadaver femur 201 with an implanted metal prosthesis 203, lying inside a water-tank. Alongside this phantom in the figure is a standard thigh phantom 205. After all the scout images are collected following the steps in FIG. 3, the set of two-dimensional scout images is converted to a set of two-dimensional sinogram images, from which a set of 2D tomographic (or cross-sectional) images will be reconstructed.

Figure 5:
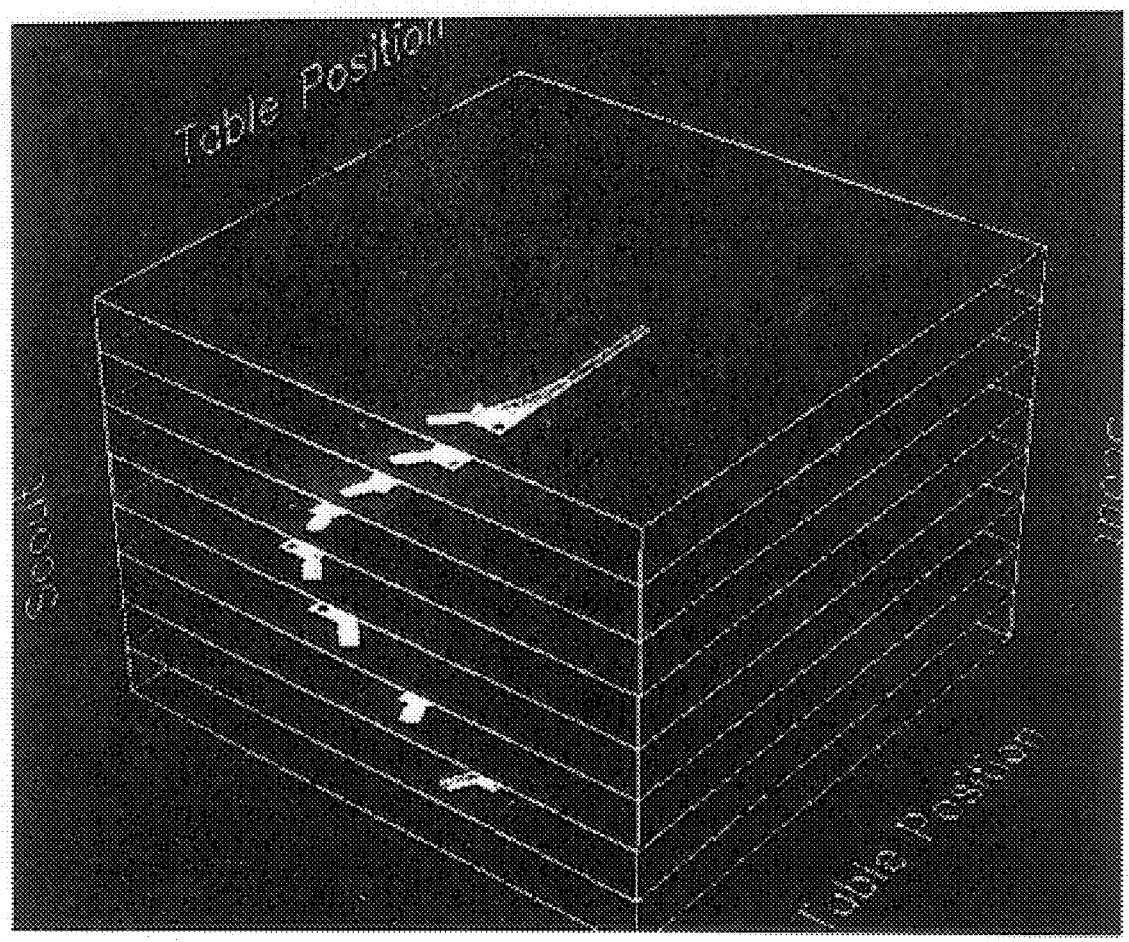
FIG. 5 shows a stack of scout images.
Figure 6:
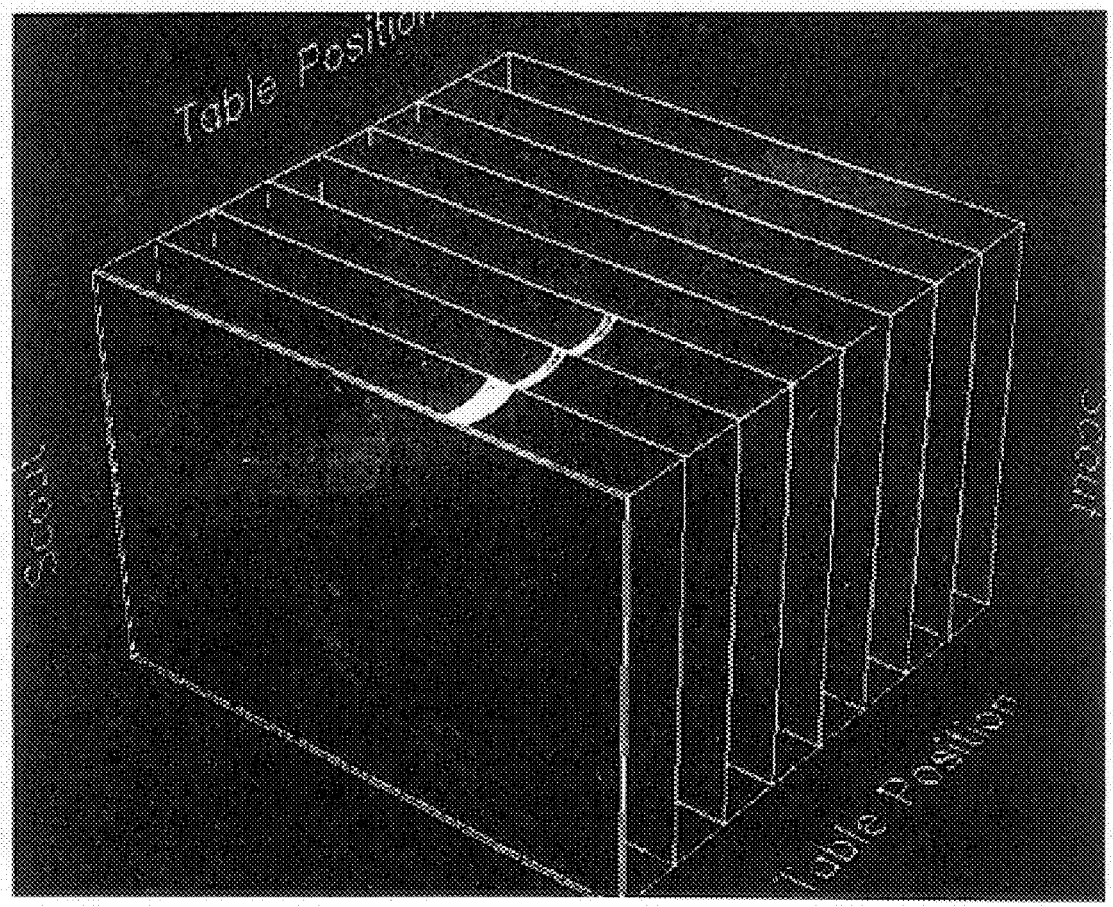
FIG. 6 is a reformatted stack of scout images.

FIGS. 5 and 6 show the relationship between scout images and sinogram data. A set of scout images, which was acquired sequentially by moving the X-ray tube around the patient, is shown stacked into a three-dimensional (3D) volume in FIG. 5. FIG. 6 shows this 3D volume sliced in the "Table Position" dimension, that is, each slice corresponds to the set of data acquired at all X-ray tube positions, at a fixed table position. This is of course equivalent to a sinogram, and the typical sinusoidal-like patterns that give a sinogram its name are easily seen.

Figure 7:
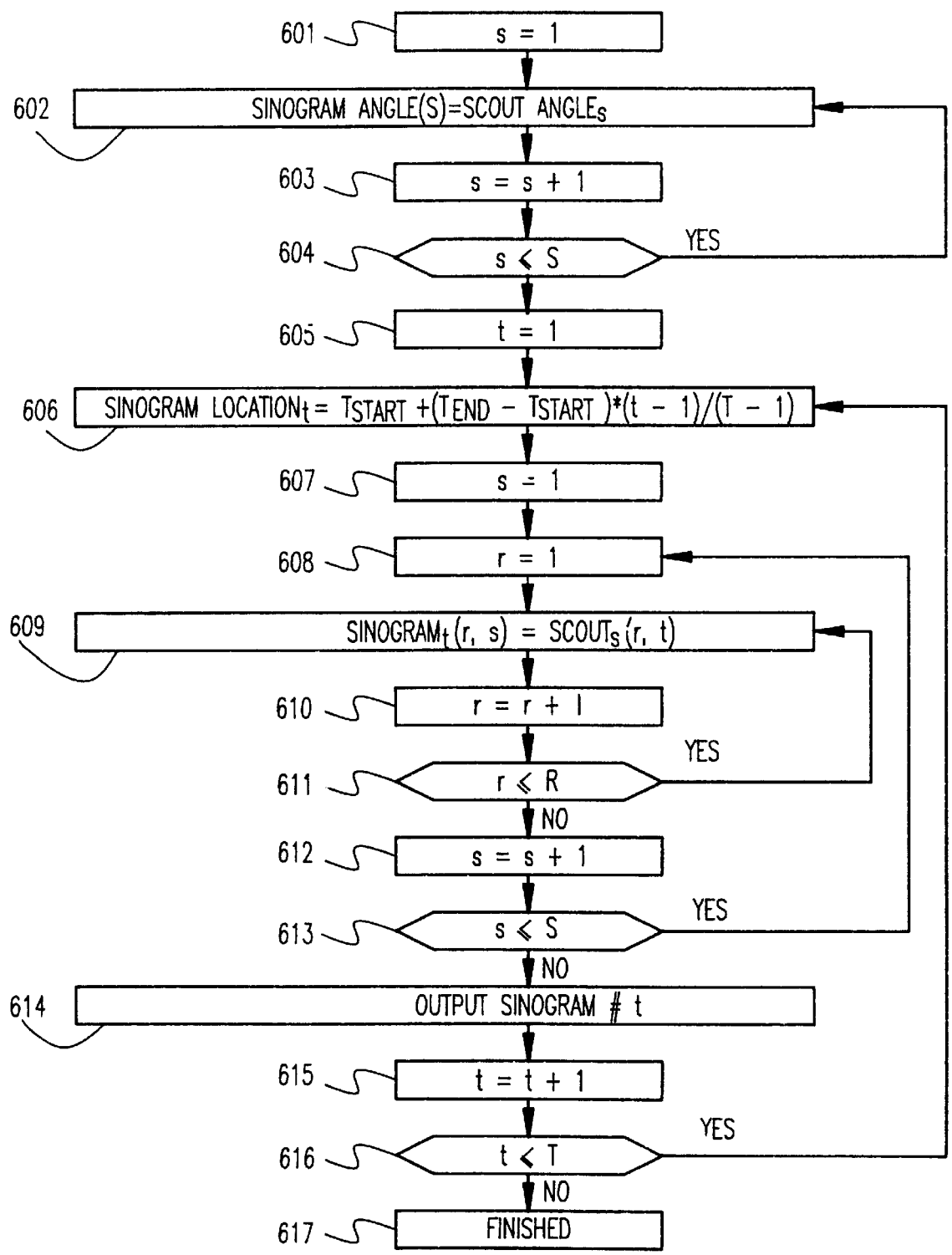
FIG. 7 is a flow chart of the steps of converting the scout data.
Figure 8:
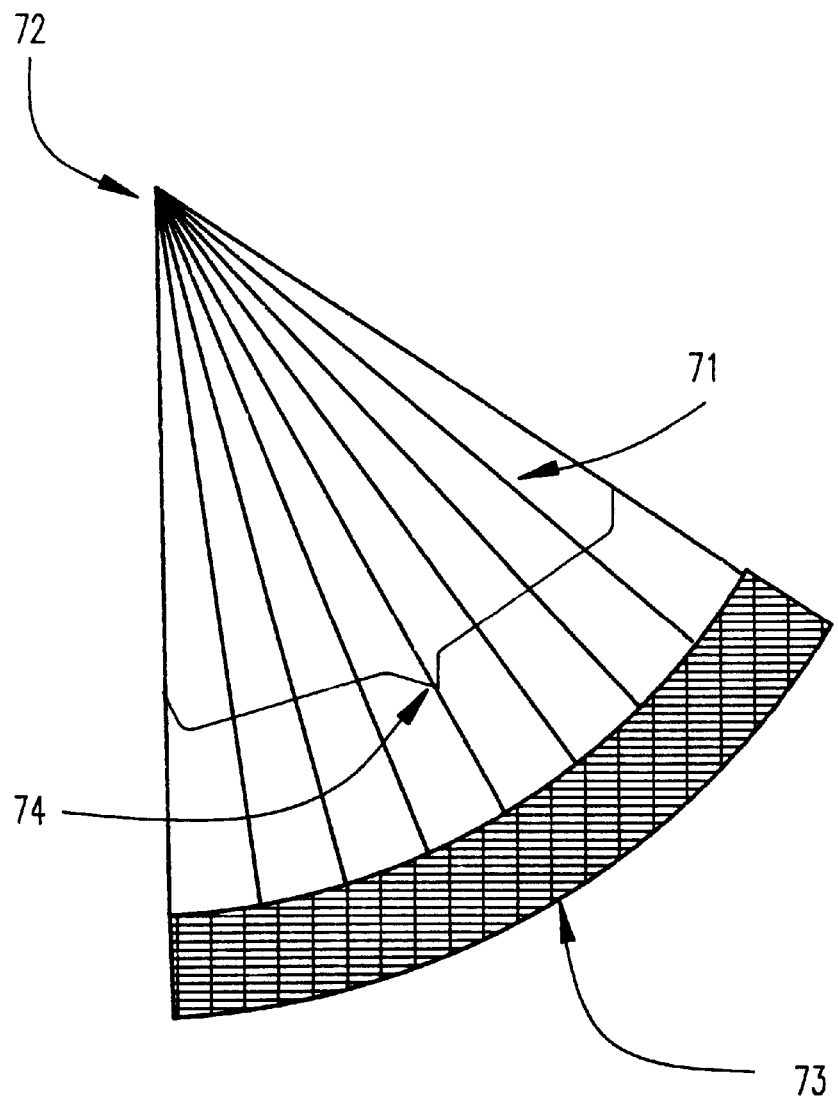
FIG. 8 is a schematic representation of a CT "view" comprising of a set of X-rays projections.

FIG. 7 shows a flow chart of the steps of converting two-dimensional scout images to two-dimensional sinogram images. For this process, S is the total number of scout images, T is the total number of projections in each scout image, and R is the total number of rays in each projection. R and T remain the same for each scout, s, in the set S. A total of T sinograms are produced from S scout images.

SCOUT_s is the two-dimensional array of size R×T representing scout image number s. Each sinogram is represented by the following three data sets:

a. SINOGRAM_t, a two-dimensional array of size R×T containing the pixel values of sinogram number t;

b. SINOGRAM ANGLE, a one-dimensional array giving the angle of the X-ray table for each projection in the sinogram; and c. TABLE POSITION_t, a single number giving the position of the scanner table during the creation of sinogram number t.

First, the one-dimensional array SINOGRAM ANGLE of size S is computed in the steps shown in blocks 601 to 604. The process begins by setting the scout image index, s, to one. In block 602 the SINOGRAM ANGLE array for s is set equal to SCOUT ANGLE_s. Then in block 603, one is added to the value of s. In block 604, if the new s value is less than or equal to S, i.e., the total number of scout images, the process repeats the steps shown in blocks 602, 603, and 604. This loop is used to calculate the values of the array SINOGRAM ANGLE.

Once the s value is greater than S, the index of the sinogram number t is set to one. This initializes the index. In the step shown in block 606, a calculation is made to divide the spacing between T_start and T_end evenly, where T_start and T_end are the start and end location of the scanner table during the creation of each scout image. With this calculation, the table location of sinogram number t is computed.

In blocks 607 and 608, s, the index of the scout image, and r, the index of the projection ray number, are initialized. Then, as shown in the step in block 609, the single array value SINOGRAM_t(r,s) is determined.

In block 610, 1 is added to the ray number, r. In block 611, it is determined whether r is less than or equal to than R. If it is, then the steps shown in block 609 through 611 are repeated.

Then in the steps shown in blocks 612 and 613, 1 is added to s, the scout image index, and a determination is made as to whether s is less than or equal to S. If it is, then the steps shown in block 608 through 613 are repeated.

Then, as shown in blocks 614, the 3 data sets, SINOGRAM_t, SINOGRAM ANGLE, and TABLE POSITION_t, which together define sinogram number t are output. Next, in the steps shown in blocks 615 and 616, 1 is added to t, the projection value, and a determination is made as to whether t is less than or equal to R. If it is, then the steps shown in block 606 through 616 are repeated. Once t is greater than T, the process is finished as shown in block 617.

Data to be Collected During Intermediate Examinations

We describe here the data to be collected during the intermediate examinations as defined above: there will usually be up to twenty-seven such examinations in the history of the patient.

D'1 A set of CT scout images. In the preferred embodiment of this invention, between four and eighteen scout images are used. In general this number can be whatever the practitioner finds will give him the best tradeoff between lowering radiation dosage and lowering the precision of the geometric model derived from the scouts and CT slices combined).

The process in D'1 is identical to the process in D1 described above.

Geometric Modeling Following Complete Examinations

In order to visualize a patient's spine in three-dimensions it suffices to deal with only vertebral bodies which are much simpler than the entire vertebra. We now explain how to combine data from D1, D2, and D3 with the three-dimensional model obtained from complete examinations in order to get satisfactory three-dimensional models of the full spine and the individual vertebrae.

Figure 9:
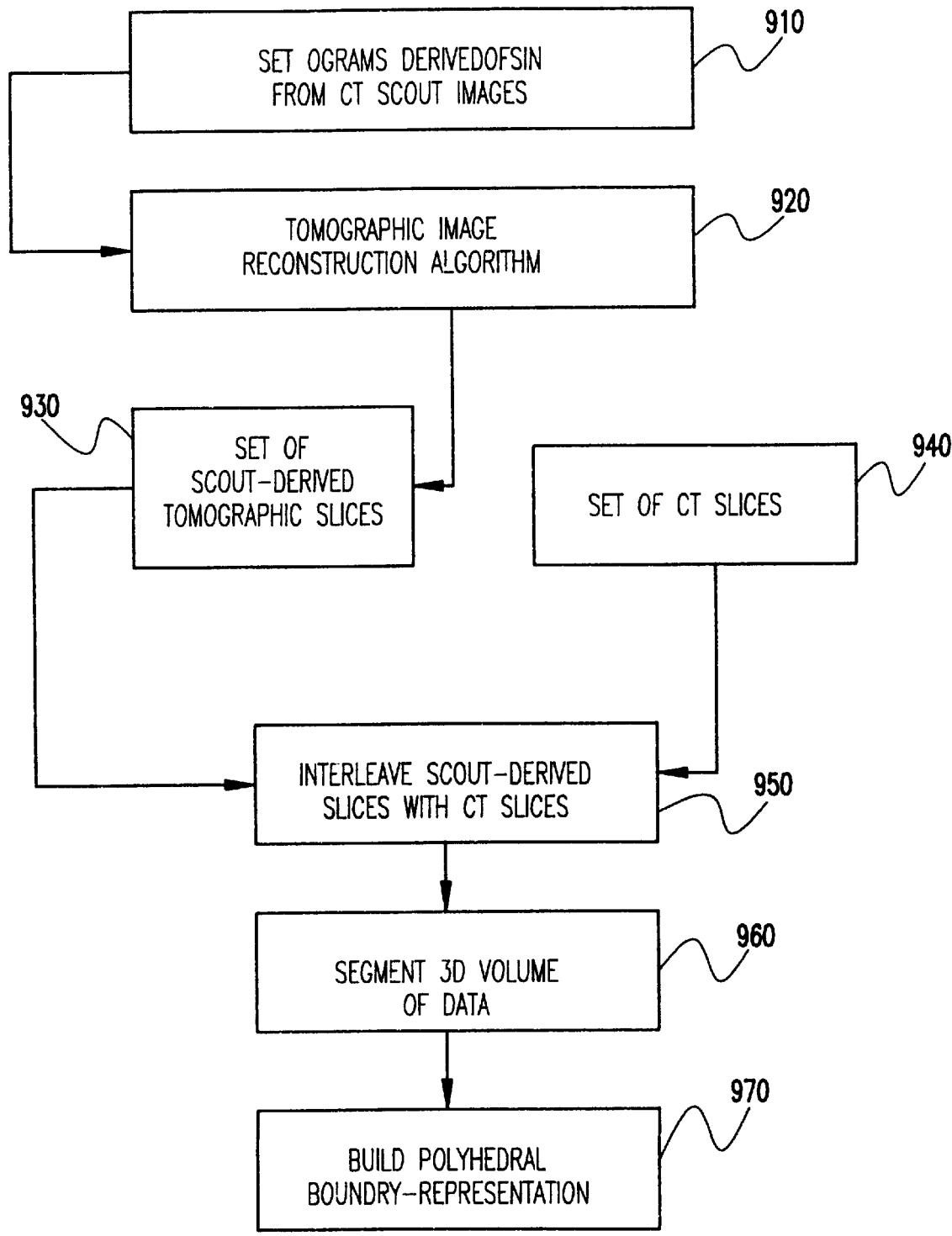
FIG. 9 is a flow chart of the steps involved in creating a 3D geometric model of a spine from the sets of the original 2D CT slices and the 2D scout images.

FIG. 9 shows the process of building a geometric model of a patient's spine from model of a spine from the sets of:
a. the original 2D CT slices, and
b. the 2D scout images.

Input block 910, contains the data produced by the process described in FIG. 7, that is, the set of sinograms that have derived from the CT scout images.

In process block 920, an "image-reconstruction-from-projections" algorithm is applied to each sinogram in 910, and producing from each sinogram, a 2D tomographic image. Any one of the many reconstruction algorithms that exist in the prior art can be used in this step (See for example the book *Image Reconstruction from Projections* by Gabor T. Herman, Academic Press, 1980). The output of process block 920 is a set of 2D scout-derived tomographic slices.

The set of 2D CT slices 940 (also 160 in FIG. 1) represents a regular sampling in 3D of the anatomy of the patient being scanned, and we can consider it to be a discrete 3D volume. The same is true of the set of 2D scout-derived tomographic slices 930. These two discrete 3D volumes are then merged into a composite 3D volume in function block 950. This composite volume will of course contain more information that either volume alone. In the preferred embodiment of this invention, this merging is done using the prior art method of bilinear interpolation (see for example the book *Computer Graphics: Principles and Practice* by James D. Foley et al. Addison-Wesley Publishing Co. 1991). In function block 960 a segmentation algorithm is applied to this composite 3D volume 950 to identify the patient's spine. This segmentation can be done using one of the many prior art segmentation methods (see for example the book *3D Imaging in Medicine: Algorithms, Systems, Applications* edited by Karl H. Hohne et al., Springer-Verlag 1990).

In function block 970, a surface-construction algorithm is applied to the segmented 3D volume 960. This algorithm will produce the required geometric model of the patient's spine in the form of a polyhedral mesh. This surface-construction can be done using one of the many prior art surface-construction methods. (See for example the book *3D Imaging in Medicine: Algorithms, Systems, Applications* edited by Karl H. Hohne et al., Springer-Verlag 1990).

This geometric model represents a simplified model of the whole spine as it appears in space. The physician is now able to study the patient's scoliotic condition, using this model together with a standard computer-graphics visualization tool.

Geometric Modeling Following Intermediate Examinations

Once the three-dimensional model for an individual has been obtained following a complete examination, it can then be used to exploit the limited data acquired from an intermediate examination to get three-dimensional pictures of the spine. Since the global spine geometry evolves faster than the individual vertebral shapes, we can assume that the gross geometry of each individual vertebra has remained essentially unchanged since the last complete examination. Therefore, we can simply create a new composite 3D volume by merging:

the 2D tomographic slices derived from the new scout images that are obtained during this current intermediate examination (as described in step D'1 above), and the set of CT slices that were obtained during the previous complete examination.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A computer-implemented method of three-dimensional modeling of objects comprising the steps of:

collecting two sets of data, each one containing a limited amount of three-dimensional spatial data of a common three-dimensional object, where the amount of data in either set alone is not sufficient to produce an adequate three-dimensional geometric model of the said common object; and combining these two sets of three-dimensional data to generate a three-dimensional model of said common object.

2. The computer-implemented method in claim 1 used for three-dimensional reconstruction of vertebral bodies of a spine by using a set of 2D computer tomography (CT) slices and a set of 2D CT scout images as the two sets of data, the set of CT slices and the set of CT scout images both having been obtained using a clinically acceptable amount of radiation.

3. The computer-implemented method in claim 2 wherein the step of combining comprises the steps of:

converting the set of CT scout images to 2D tomographic slices using a tomographic reconstruction algorithm;

creating a 3D volume by interleaving the tomographic slices and the set of CT slices;

segmenting an object of interest; and creating a geometric model of the object of interest.

4. A computer system used to improve the geometric modeling of three-dimensional objects by utilizing two complementary sets of three-dimensional data comprising:

a computer with a memory, a central processing unit (CPU), and a display monitor;

a first data structure resident in said memory and containing a limited amount of three-dimensional data of the shape of a three-dimensional object, where the amount of data in this first data set is not sufficient on its own to allow construction of a satisfactory geometric model of this three-dimensional object;

a second data structure resident in said memory and containing a limited amount of three-dimensional data of the shape of the said three-dimensional object, where the amount of data in this second data set is not sufficient on its own to allow construction of a satisfactory geometric model of this said three-dimensional object; and a process executed by the CPU, to construct a three-dimensional model of the said object using both and the three-dimensional data sets.

5. The computer system in claim 4 used for three-dimensional reconstruction of the vertebral bodies of the spine by using a set of 2D computer tomography (CT) slices, and a set of 2D CT scout images, as the two sets each having a limited amount of three-dimensional data of a common object, the set of CT slices and the set of CT scout images both having been obtained using a clinically acceptable amount of radiation.

* * * * *